(12) United States Patent
Zaleski

(10) Patent No.: US 9,837,257 B2
(45) Date of Patent: Dec. 5, 2017

(54) METHOD AND DEVICE FOR A COATED CORONA IONIZATION SOURCE

(71) Applicant: Smiths Detection Montreal Inc., Mississauga, Ontario (CA)

(72) Inventor: Henryk Zaleski, Scarborough (CA)

(73) Assignee: Smiths Detection Montreal Inc., Mississauga, Ontario (CA)

(*) Notice: Subject to any disclaimer, the term of this patent is extended or adjusted under 35 U.S.C. 154(b) by 0 days.

(21) Appl. No.: 14/900,539

(22) PCT Filed: Jun. 19, 2014

(86) PCT No.: PCT/CA2014/050574
§ 371 (c)(1),
(2) Date: Dec. 21, 2015

(87) PCT Pub. No.: WO2014/201564
PCT Pub. Date: Dec. 24, 2014

(65) Prior Publication Data
US 2016/0155623 A1    Jun. 2, 2016

Related U.S. Application Data

(60) Provisional application No. 61/837,785, filed on Jun. 21, 2013.

(51) Int. Cl.
*H01J 49/16*    (2006.01)
*H01J 27/26*    (2006.01)
*G01N 27/62*    (2006.01)

(52) U.S. Cl.
CPC .......... *H01J 49/168* (2013.01); *G01N 27/622* (2013.01); *H01J 27/26* (2013.01)

(58) Field of Classification Search
USPC .................. 250/288, 423 R, 424, 423 F
See application file for complete search history.

(56) References Cited

U.S. PATENT DOCUMENTS 4,409,604 A    10/1983   Fotland
4,585,323 A     4/1986   Ewing et al.
(Continued)

FOREIGN PATENT DOCUMENTS

CA    2533311 A1    2/2005
CA    2839405 A1   12/2012
(Continued)

OTHER PUBLICATIONS

Extended European Search Report dated Jan. 20, 2017 for EP Appln. No. 14813907.4.
(Continued)

*Primary Examiner* — Kiet T Nguyen
(74) *Attorney, Agent, or Firm* — Advent, LLP

(57) ABSTRACT

A corona ionization source assembly and fabrication methods are described that include a fine wire including a wire core including a first material, and a wire coating including a second material, where the wire coating surrounds a portion of the wire core, and the diameter of the wire coating is greater than the diameter of the wire core. Additionally, the fine wire may be coupled to a mounting post. In an implementation, a process for fabricating the corona ionization source assembly that employs the techniques of the present disclosure includes forming a wire core, forming a wire coating that surrounds the wire core, forming a mask layer on at least a portion of the wire coating, etching the wire coating, and removing the mask layer from the wire coating.

19 Claims, 4 Drawing Sheets

(56) References Cited

U.S. PATENT DOCUMENTS

| | | |
|---|---|---|
| 4,933,108 A | 6/1990 | Soredal |
| 5,510,879 A * | 4/1996 | Facci .................. G03G 15/0208 361/225 |
| 5,684,300 A * | 11/1997 | Taylor .................. G01N 27/622 250/286 |
| 2014/0246581 A1* | 9/2014 | Levin .................. G01N 27/622 250/288 |

FOREIGN PATENT DOCUMENTS

| | | |
|---|---|---|
| WO | 8702451 A1 | 4/1987 |
| WO | 2009111149 A1 | 9/2009 |

OTHER PUBLICATIONS

International Search Report dated Aug. 22, 2014 for PCT/CA2014/050574.

* cited by examiner

METHOD AND DEVICE FOR A COATED CORONA IONIZATION SOURCE

REFERENCE TO RELATED APPLICATION

This application claims priority to U.S. Provisional Patent Application Ser. No. 61/837,785 entitled "Method and Device for a Coated Corona Ionization Source" filed Jun. 21, 2013, which is incorporated by reference.

BACKGROUND

Ion mobility spectrometers (IMS) can identify material from a sample of interest by ionizing the material (e.g., molecules, atoms, etc.) and measuring the time it takes the resulting ions to reach a detector. The ion's time of flight is associated with its ion mobility that relates to the mass and geometry of the molecule that was ionized. Ion mobility spectrometry operates at around ambient atmospheric pressure and separates ions with respect to mobility in the presence of a drift gas. The detector's output can be visually represented, for example, as a plasmagram of peak height versus drift time.

Mass spectrometers (MS) operate in a vacuum and separate ions with respect to charge/mass ratio. In some embodiments using a mass spectrometer, a sample, which may be solid, liquid, or gas, is ionized. The ions are separated in a mass analyzer according to mass-to-charge ratio and are detected by a device capable of detecting charged particles. The signal from the detector is then processed into the spectra of the relative abundance of ions as a function of the mass-to-charge ratio. The atoms or molecules are identified by correlating known masses by the identified masses or through a characteristic fragmentation pattern.

Each detection system may include a sample source, an ion source, an analyzer, and a detector. Some examples of ion sources, which may include a device that creates charged particles (the ions), may include electrospray ionization, inductively-coupled plasma, spark ionization, a radioactive source (e.g., $^{63}$Ni), etc.

SUMMARY

A corona ionization source assembly and methods for fabricating the corona ionization source assembly are described that include a fine wire including a wire core including a first material, and a wire coating including a second material, where the wire coating surrounds a portion of the wire core, and the diameter of the wire coating is greater than the diameter of the wire core, and a post coupled to the fine wire. In an implementation, a process for fabricating the corona ionization source assembly that employs the techniques of the present disclosure includes forming a wire core, forming a wire coating that surrounds the wire core, forming a mask layer on at least a portion of the wire coating, etching the wire coating, and removing the mask layer from the wire coating.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Icon The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION

Figure 1A:
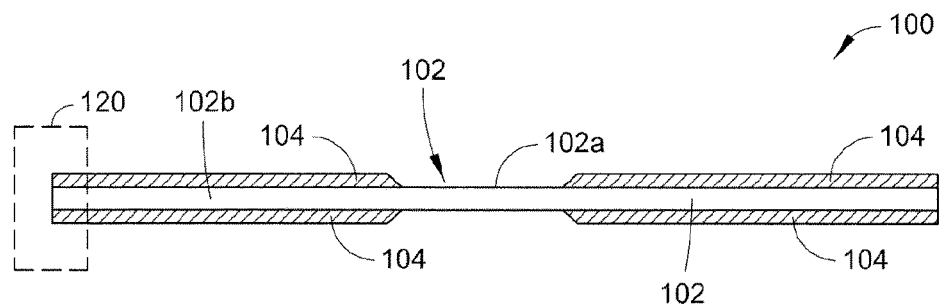
FIG. 1A is an illustration of a corona ionization source assembly configured to implement a fine wire in accordance with the present disclosure.

In ion mobility spectrometry, a spectrometer may include a sample source, an ion source, an analyzer, and a detector. One type of ionization source often used includes a corona source. A corona source utilizes an electrical discharge brought on by the ionization of a fluid surrounding a conductor that is electrically energized. The electrical discharge from the corona source will occur when the strength (i.e., potential gradient) of the electric field around the conductor is high enough to form a conductive region, but not high enough to cause electrical breakdown or arcing to nearby objects.

One type of corona source is a point corona. It includes a very fine wire (e.g., 10 μm or less) connected to a high voltage source (e.g., from 500 V to a few kV). The high voltage applied to the fine wire creates a field around the fine wire. Because of the small dimension of the wire, the field around the tip of the wire is very strong and causes air and/or another gas to ionize. The field strength rapidly decreases with increasing distance from the point of the wire, which prevents arcing.

Another type of corona is a wire corona. A wire corona may include a fine wire disposed between two posts or supports. When a high voltage is applied to the fine wire, a strong electrical field is created in the vicinity of the fine wire, which ionizes the surrounding gas thereby creating ions to be analyzed by the spectrometer. The wire can also be heated by applying electrical current through the wire. A hot wire corona, such as the one described, can more reliably operate and requires a lower high voltage for operation. The high voltage applied to the fine wire may be a constant voltage (e.g., DC power), alternating voltage (e.g., AC power) or a series of pulses.

However, fabricating such a corona source has proven difficult because of the complex attachment process of the fine wire to the posts while providing a reliable electrical connection. Generally, a small diameter wire requires a lower high voltage to be applied to generate corona, which provides a more efficient spectrometer. However, small diameter wires are very fragile and difficult to handle and attach to a post. Previous fabrication methods using crimping (too much crimping would break the wire, too little crimping would not provide good electrical contact), welding (welding a fine wire is very difficult), or soldering (the solder would melt at the operating temperature of the corona) have been unreliable. Often, the wire diameter is a compromise between operation and ability to manufacture the assembly. For a hot wire corona, providing reliable electrical contact to the fine wire presents additional difficulty.

Accordingly, a corona ionization source assembly and fabrication methods are described that include a fine wire including a wire core including a first material, a wire coating including a second material where the wire coating surrounds a portion of the wire core and the diameter of the wire coating is greater than the diameter of the wire core, and a post that is coupled to the fine wire. In an implementation, a process for fabricating the corona ionization source assembly that employs the techniques of the present disclosure includes forming a wire core, forming a wire coating that surrounds the wire core, forming a mask layer on at least a portion of the wire coating, etching the wire coating, and removing the mask layer from the wire coating.

Figure 1B:
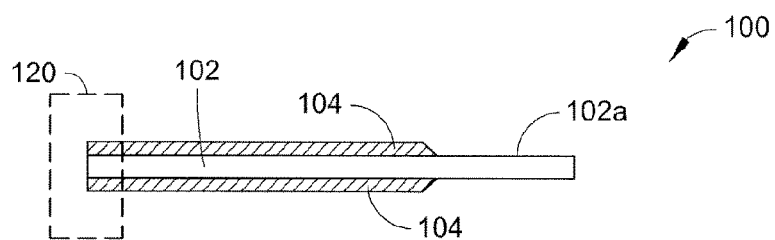
FIG. 1B is an illustration of a corona ionization source assembly configured to implement a fine wire in accordance with the present disclosure.
Figure 1C:
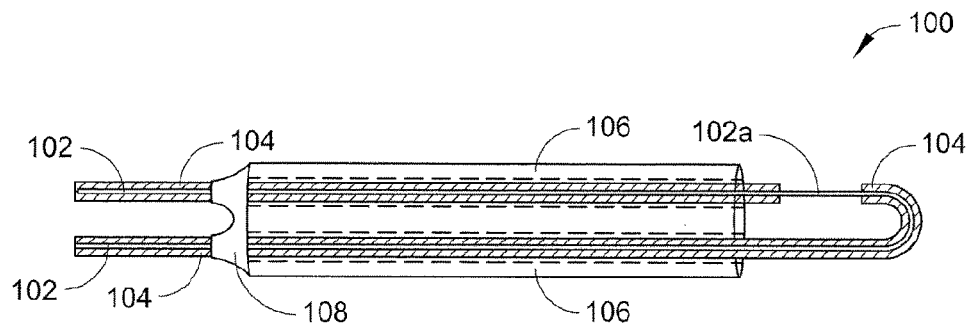
FIG. 1C is an illustration of a corona ionization source assembly configured to implement a fine wire in accordance with the present disclosure.

FIGS. 1A through 1C illustrate a corona source assembly 100 in accordance with example implementations of the present disclosure. As shown, the corona source assembly 100 includes a fine wire 102. The fine wire 102 includes a wire filament 102a and a wire core 102b. In implementations, the fine wire 102 is fabricated as discussed below and coupled (e.g., by crimping, soldering, welding, etc.) to a mounting post 120, which functions as a mechanical support for the fine wire 102. Additionally, the fine wire includes a wire that is of a smaller diameter (e.g., from less than 1 µM to over 100 µm) than a wire coating 104 subsequently formed on the fine wire 102. In one implementation, the fine wire 102 includes a platinum-rhodium alloy with a diameter of about 50 µm. In other implementations, the fine wire 102 may include platinum, platinum alloys, gold, iridium, tungsten, alloys, other metals, etc. The material used for the fine wire 102 may include a first material. In implementations, the corona forms around and adjacent to the wire filament 102a, where the wire filament 102a includes the portion of the fine wire 102 that is exposed to a sample to be ionized as a high voltage is applied. In implementations, the wire core 102b includes the portion of the fine wire 102 that is covered and/or surrounded by the wire coating 104. The fine wire 102 may be coupled to a mounting post 120, where the post 120 is configured to provide mechanical support as well as an electrical connection. The mounting post 120 may include a metal or an alloy. In some implementations, the mounting post 120 may include a separate structure from the corona source assembly 100. In other implementations, the mounting post 120 may include a portion of the fine wire 102 covered by the wire coating 104 (e.g., a portion thicker than the portion designed as the corona source), such as the embodiment shown in FIG. 1C.

As shown in FIGS. IA through 1C, the corona source assembly 100 includes a wire coating 104 fabricated of a second material. In embodiments, the wire coating 104 surrounds at least a portion of the fine wire 102. In these embodiments, the diameter of the wire coating 104 is greater than the diameter of the fine wire 102. In one implementation, the wire coating 104 includes a coating of nickel-cobalt alloy (NiColoy) that surrounds at least a portion of the fine wire 102. In other implementations, the wire coating 104 includes other materials and/or metals, such as copper, nickel, iron, other metals or alloys, etc. In one specific implementation, the wire coating 104 has a diameter of about 100 µm. In another specific implementation, the wire coating 104 has a diameter of about one millimeter. The wire coating 104 may include other diameters and thicknesses as long as the diameter of the wire coating 104 is larger than the diameter of the fine wire 102. Additionally, the material of the wire coating 104 has different chemical properties than the material of the fine wire 102.

FIG. 1A illustrates one example of a straight configuration of a corona source assembly 100. In this configuration, the wire filament 102a is formed as a portion of and/or securely coupled to two thicker wires (e.g., two different portions of the fine wire 102 covered with the wire coating 104 with the wire filament 102a between the two different portions, where the high voltage power can flow through the wire filament 102a, and a sample to be ionized is exposed to the wire filament 102a and resulting corona). FIG. 1B illustrates an example of a point corona source assembly 100. In this configuration, the wire coating 104 and the fine wire 102 may be formed similarly to the straight configuration except that one end of the fine wire 102 is formed as a projecting point (e.g., one end of the fine wire 102 is not coupled to another wire). In this configuration, a high voltage is applied to the fine wire 102 and a corona is formed around the projecting point.

One example of a hot wire corona source assembly 100 for an ion mobility spectrometry device is illustrated in FIG. 1C. In this specific example, a fine wire 102 includes a thin platinum-rhodium wire filament 102a that is securely attached to two thicker wires (e.g., portions of the fine wire 102 that are covered by a wire coating 104). The thick wires can be used to mechanically secure the fine wire 102 and to provide electrical contacts. This specific example includes an etched wire coating 104 and fine wire 102 and a portion of the coated wire that is bent into a desired shape. When the coated wire is bent, the etching process can be performed prior to or subsequent to the bending or shaping process depending on the desired configuration and material used. In this example, a portion of the fine wire 102 and the wire coating 104 are covered by or surrounded by a ceramic tube 106. The ceramic tube 106 may function as mechanical support while additionally functioning as an electrical insulator. Additionally, the ceramic tube 106 may be coupled to a portion of the wire coating 104 by ceramic cement 108 or other suitable adhesive. In this example, the corona source assembly 100 may be further coupled to a mounting post 120.

Figure 1D:
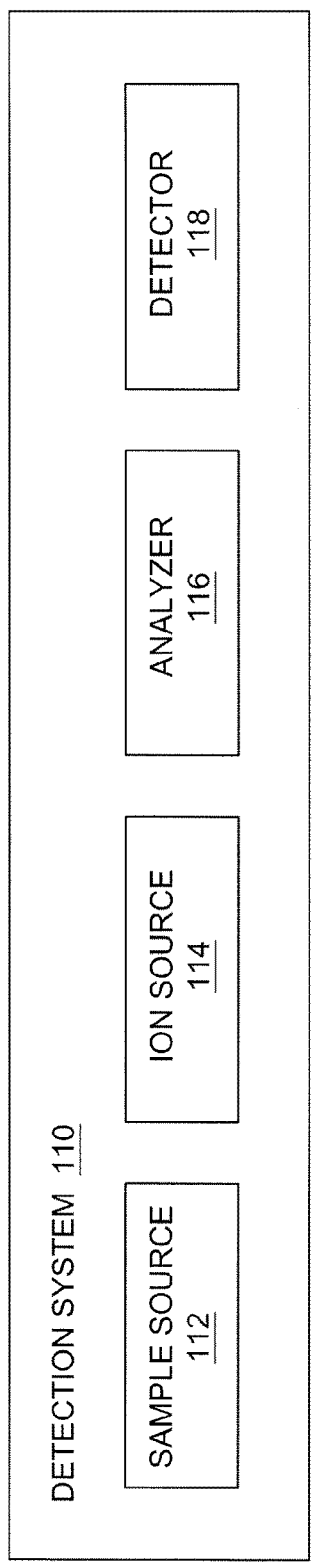
FIG. 1D is a diagrammatic illustration of an example detection system in accordance with the present disclosure.

As shown in FIG. 1D, the corona source assembly 100 may be utilized as a component in a detection system 110 to function as an ion source 114. In one embodiment, a detection system 110 may include a sample source 112, an ion source 114 (e.g., the corona source assembly 100), an analyzer 116, and a detector 118. In this embodiment, a sample may be introduced to the sample source 112 of a detection system 110 and may be converted to a desired form (e.g., conversion of a liquid to a gas). The sample may then be exposed to the ion source 114, which creates the sample into charged particles, or ions. In one embodiment using a mass spectrometer (e.g., in Atmospheric Pressure Ionization (API) mode), the ions are created near ambient pressure and then introduced to the analyzer 116 through a capillary and/or an orifice. In this embodiment, the ions are then separated using an analyzer 116 according to their mass-to-charge ratios. In another embodiment using an ion mobility spectrometer, the ions are created by a corona and introduced to the analyzer 116, which are then separated according to their mobilities. Finally, the detector 118 measures the value of an indicator quantity and thus provides data for calculating the abundance of each ion present.

Figure 2:
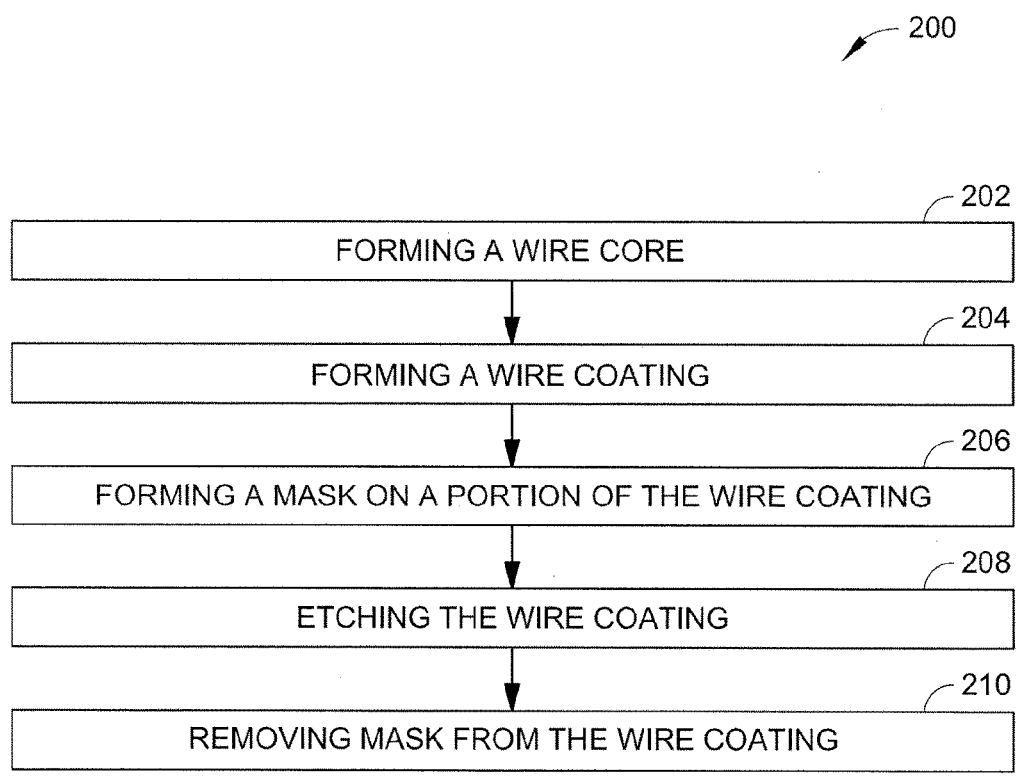
FIG. 2 is a flow diagram depicting a process in an example implementation for fabricating a corona ionization source assembly, such as the device shown in FIGS. 1A through 1D.

FIG. 2 illustrates an example process 200 that employs the disclosed techniques to fabricate a corona source assembly, such as the corona source assembly 100 shown in FIGS. 1A through 1C. FIGS. 3A through 3D illustrate sections 300 of an example corona source assembly 100 that is utilized in ion mobility spectrometers and/or mass spectrometers (such as detection system 110 shown in FIG. 1D).

Figure 3A:
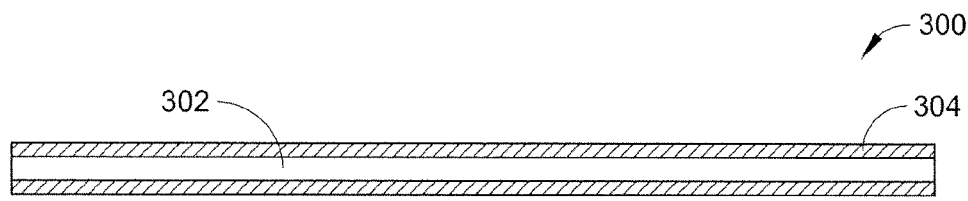
FIGS. 3A through 3D are diagrammatic partial cross-sectional side elevation views illustrating the fabrication of a corona ionization source assembly, such as the device shown in FIGS. 1A through 1D, in accordance with the process shown in FIG. 2.

Accordingly, a wire core is formed (Block 202). FIG. 3A illustrates forming a portion of a fine wire 302. In implementations, forming the wire core 302 may include drawing a metal through a hole in a die or draw plate to form the wire core 302 or fine wire. In one embodiment, forming a wire core 302 (i.e., fine wire 102) includes drawing a platinum-rhodium alloy through a hole in a die plate to form a wire with a diameter of about 50 µm. In other embodiments, forming a wire core includes drawing other metals (e.g., platinum alloy, gold, iridium, tungsten, etc.) through a die plate or a hole in a die to form a wire core 302 with a diameter of about 50 µm. The wire core 302 may be formed with additional diameters and sizing (e.g., anywhere from less than about 1 µm to greater than about 100 µm).

Next, a wire coating is formed on the wire core (Block 204). FIG. 3A illustrates forming a wire coating 304 on the wire core 302. In implementations, the wire coating 304 may be deposited on the wire core 302 using a variety of methods, for example, electroplating, vapor deposition, plasma deposition, etc. In one specific embodiment, a wire coating 304 is formed on the wire core 302 by electroplating NiColoy on a platinum-rhodium wire core 302 to a desired diameter. In another embodiment, a thick wire core 302 (e.g., about 0.5 mm) is inserted into a tube of the wire coating 304 and the combination wire core 302 and wire coating 304 is drawn using a standard wire-drawing technology. In these embodiments, the thicknesses and dimensions of the wire coating 304 and/or the wire core 302 may be varied depending on the desired final configuration.

Figure 3B:
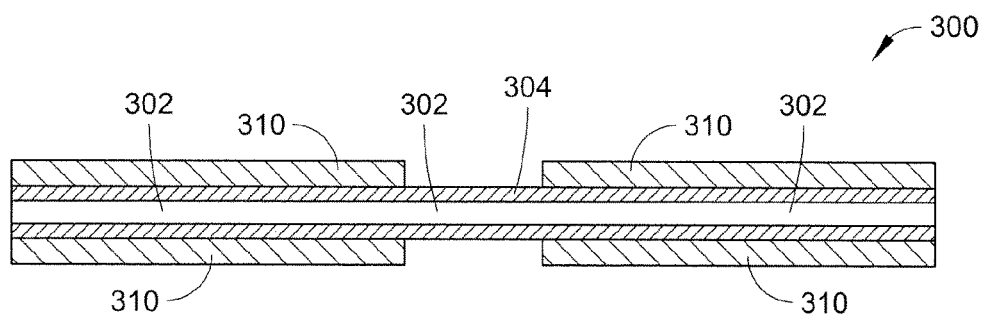

Next, a mask layer is formed on at least a portion of the wire coating (Block 206). FIG. 3B illustrates depositing a mask layer 310 on at least a portion of the wire coating 304. In implementations, forming the mask layer 310 includes forming an etch-resistant coating. Forming the mask layer 310 on the wire coating 304 may include using standard photolithography and deposition methods. Some examples of depositing the mask layer 310 may include using chemical deposition (e.g., chemical vapor deposition), physical deposition (e.g., sputtering), spraying, coating, etc. Photolithography may include patterning parts of a light-sensitive thin film (e.g., the mask layer 310) using light to transfer a geometric pattern from a photomask to the thin film on the wire coating 304. The mask layer 310 is designed to be etch-resistant so that the portion of the wire coating 304 that is not covered by the mask layer 310 is the only portion of either the mask layer 310 or the wire coating 304 that is subject to removal by an etchant. In one implementation, a mask layer 310 is formed on a portion of the wire coating 304 that is not intended to be removed while the mask layer 310 is not formed on a portion of the wire coating designed to be removed.

Figure 3C:
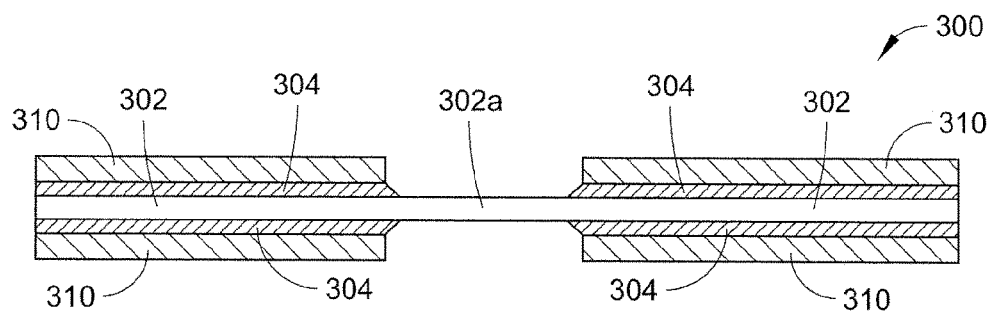

Next, the wire coating is etched (Block 208). FIG. 3C illustrates subjecting the wire coating 304 and the mask layer 310 to an etchant. Etching may include chemically removing layers (e.g., the wire coating 304) from the surface of the wire core 302 during manufacturing. Different etchants may be used, such as a wet etchant (e.g., buffered hydrofluoric acid, potassium hydroxide, aqua regia, hydrochloric acid, etc.), or a plasma etchant, depending on the material used as the wire coating 304. In implementations, the etchant is selected to remove only the wire coating 304 while leaving the wire core 302 intact. In one embodiment, a mask layer 310 is deposited and patterned on the wire coating 304 so that the portion of the wire coating 304 disposed over the portion of the wire filament 302a to be exposed is the only portion of the wire coating 304 that is exposed to the etchant. In this embodiment, the wire coating 304 is exposed to the etchant and removed, while the portion of the mask layer 310 that is exposed to the etchant is unaffected. In one specific implementation, a wire coating of NiColoy is etched using a nitric acid etchant. In some embodiments, the wire core 302 is unaffected by the etchant (e.g., the diameter of the wire core 302 is substantially constant). In other specific embodiments, a portion of the wire core 302 may be removed by an etchant, which may provide a thinner portion of the wire core 302 (e.g., the diameter of the wire filament 302a is smaller than the other portion of the wire core 302).

Figure 3D:
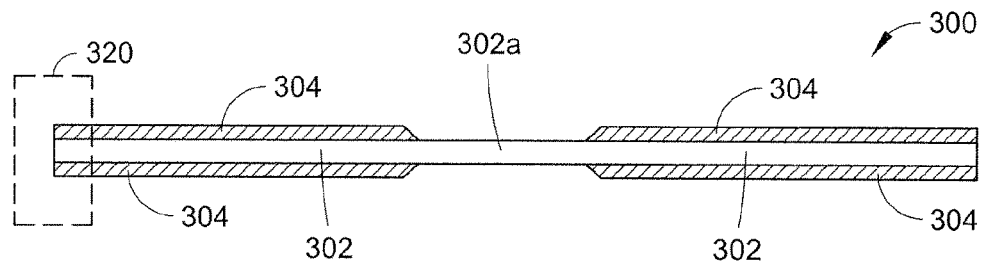

The mask layer is then removed from the wire coating (Block 210). FIG. 3D illustrates removing the mask layer 310 from the wire coating 304. After the mask layer 310 is no longer needed, it must be removed from the wire coating 304 while leaving the wire coating 304 substantially intact. In one embodiment, removing the mask layer 310 includes using a liquid mask layer 310 stripper, which chemically alters the mask layer 310 so that it no longer adheres to the wire coating 304. In some specific embodiments, the mask layer 310 may be removed by a plasma containing oxygen, which oxidizes the mask layer 310. Subsequent to fabricating the corona source assembly 100, the corona source assembly 100 may be further processed as needed for inclusion in a detection system (e.g., ion mobility spectrometer or mass spectrometer). Additionally, the corona source assembly 100 may be further attached to a mounting post 320 (e.g., welding, crimping, soldering, etc.) for further mechanical support and/or electrical connection.

Although the invention has been described in language specific to structural features and/or methodological acts, it is to be understood that the invention defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claimed invention.

What is claimed is:

1. A corona ionization source assembly, comprising:
a fine wire, including
a wire core including a first material comprising a platinum-rhodium alloy wire; and
a wire coating including a second material, where the wire coating surrounds a portion of the wire core, and the diameter of the wire coating is greater than the diameter of the wire core.

2. The corona ionization source assembly of claim 1, wherein the wire core comprises a wire core with a diameter less than about 100 µm.

3. The corona ionization source assembly of claim 1, wherein the wire coating including a second material comprises a wire coating with a diameter of at least about 100 µm.

4. The corona ionization source assembly of claim 1, further comprising the fine wire coupled to at least one mounting post.

5. The corona ionization source of claim 1, wherein the wire coating including a second material comprises a nickel-cobalt alloy.

6. A corona ionization source assembly, comprising:
a fine wire, including
a wire core including a first material; and
a wire coating including a second material, the wire coating surrounding a portion of the wire core, the diameter of the wire coating being greater than the diameter of the wire core, the second material comprising a nickel-cobalt alloy.

7. The corona ionization source of claim 6, wherein the wire core including a first material comprises a platinum-rhodium alloy wire.

8. The corona ionization source of claim 6, wherein the wire core comprises a wire core with a diameter less than about 100 μm.

9. The corona ionization source of claim 6, wherein the wire coating including a second material comprises a wire coating with a diameter of at least about 100 μm.

10. The corona ionization source of claim 6, further comprising the fine wire coupled to at least one mounting post.

11. A detection system, comprising:
a corona ionization source assembly comprising a fine wire, including
a wire core including a first material comprising a platinum-rhodium alloy wire;
a wire coating including a second material, where the wire coating surrounds a portion of the wire core, and the diameter of the wire coating is greater than the diameter of the wire core;
an analyzer; and
a detector.

12. The detection system of claim 11, wherein the wire core comprises a wire core with a diameter less than about 100 μm.

13. The detection system of claim 11, wherein the wire coating including a second material comprises at least one of copper, nickel, iron, or a metal alloy.

14. The detection system of claim 11, including at least one of an ion mobility spectrometer system or a mass spectrometer system.

15. The detection system of claim 11, wherein the wire coating including a second material comprises a nickel-cobalt alloy.

16. A detection system, comprising:
a corona ionization source assembly comprising a fine wire, including
a wire core including a first material;
a wire coating including a second material, where the wire coating surrounds a portion of the wire core, and the diameter of the wire coating is greater than the diameter of the wire core, the second material comprising a nickel-cobalt alloy;
an analyzer; and
a detector.

17. The detection system of claim 16, wherein the wire core including a first material comprises a platinum-rhodium alloy wire.

18. The detection system of claim 16, wherein the wire core comprises a wire core with a diameter less than about 100 μm.

19. The detection system of claim 16, including at least one of an ion mobility spectrometer system or a mass spectrometer system.

* * * * *